United States Patent [19]

Kasprzyk et al.

[11] Patent Number: 5,035,694
[45] Date of Patent: Jul. 30, 1991

[54] DILATATION CATHETER ASSEMBLY WITH HEATED BALLOON

[75] Inventors: Daniel J. Kasprzyk; Jean C. Orth, both of Sunnyvale; John W. Gaiser, Mountain View, all of Calif.

[73] Assignee: Advanced Cardiovascular Systems, Inc., Santa Clara, Calif.

[21] Appl. No.: 351,777

[22] Filed: May 15, 1989

[51] Int. Cl.⁵ .................................... A61M 29/02
[52] U.S. Cl. ........................... 606/27; 606/192; 606/194; 606/28; 606/96
[58] Field of Search ............. 606/192, 194, 27, 30–33, 606/7, 159; 604/95, 96

[56] References Cited

U.S. PATENT DOCUMENTS

| | | | |
|---|---|---|---|
| 4,552,127 | 11/1985 | Schiff | 606/192 X |
| 4,641,649 | 2/1987 | Walinsky | 606/33 |
| 4,643,186 | 2/1987 | Rosen et al. | 606/159 X |
| 4,654,024 | 3/1987 | Crittenden et al. | 606/31 X |
| 4,672,962 | 6/1987 | Hershenson | 606/28 |
| 4,709,698 | 12/1987 | Johnston et al. | 128/303.12 |
| 4,754,752 | 7/1988 | Ginsburg | 128/303.12 |
| 4,799,479 | 1/1989 | Spears | 128/303.1 |
| 4,808,164 | 2/1989 | Hess | 606/194 X |

Primary Examiner—Mickey Yu
Assistant Examiner—Kerry Owens
Attorney, Agent, or Firm—Fulwider, Patton, Lee & Utecht

[57] ABSTRACT

A balloon dilatation catheter having means to raise the temperature of the working surface of the balloon while the balloon is being inflated during an angioplasty procedure. In one embodiment, the balloon is provided with a thin electrically conductive layer in heat transfer relationship therewith preferably on the interior surface of the balloon. Electrical power at radio frequencies is preferred and a coaxial cable is employed to deliver such power to a conductive layer for heating the balloon. In another embodiment, the balloon itself is formed of electrically conductive material. A perfusion lumen may be provided through the balloon with one or more proximal inlet ports and one or more distal discharge ports in fluid communication with the lumen to allow blood to pass through the balloon when it is inflated during angioplasty procedures. This facilitates the flow of oxygenated blood distally of the catheter when the balloon is inflated thus allowing for extended balloon inflations, e.g., up to 30 minutes or more.

29 Claims, 4 Drawing Sheets

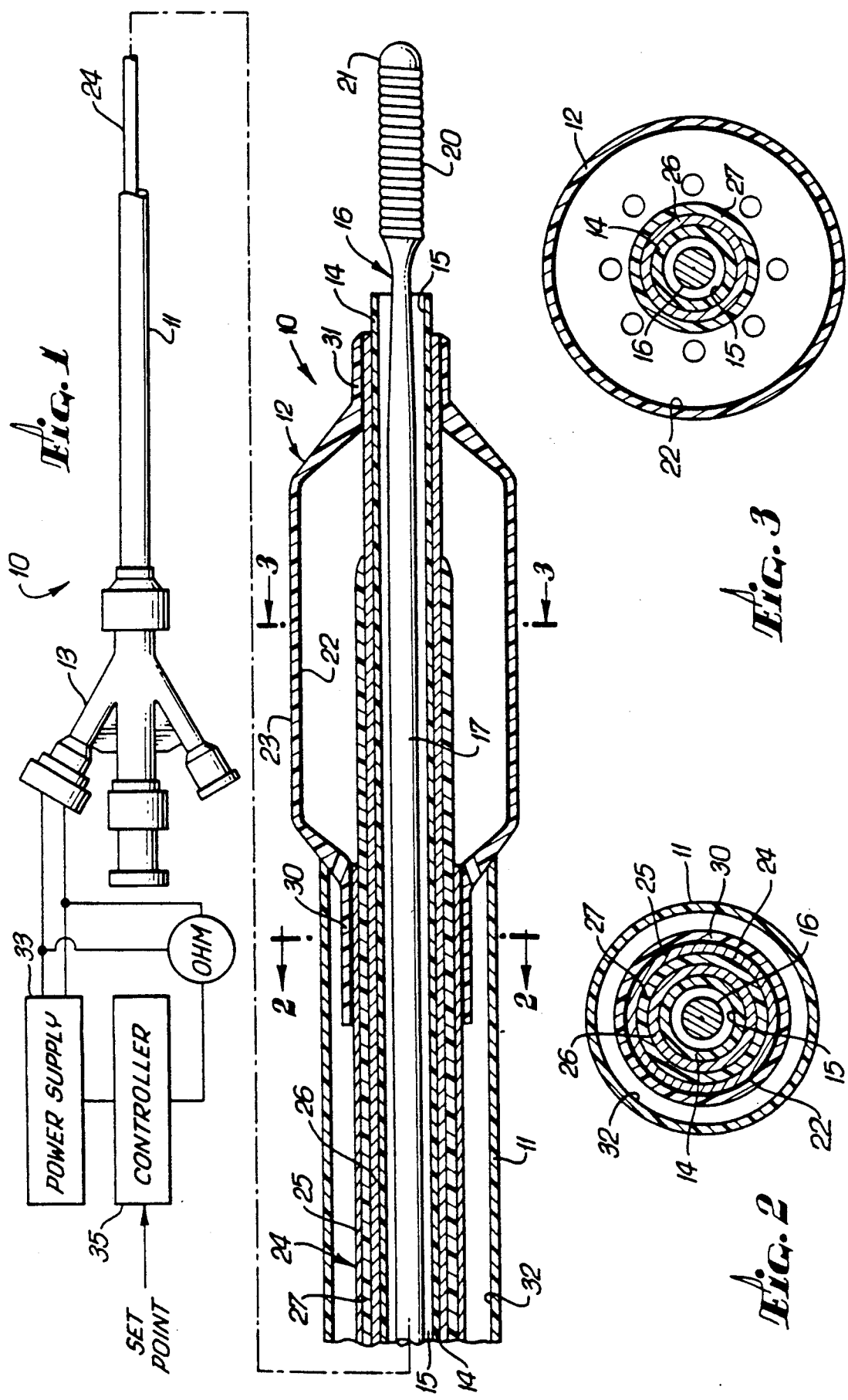

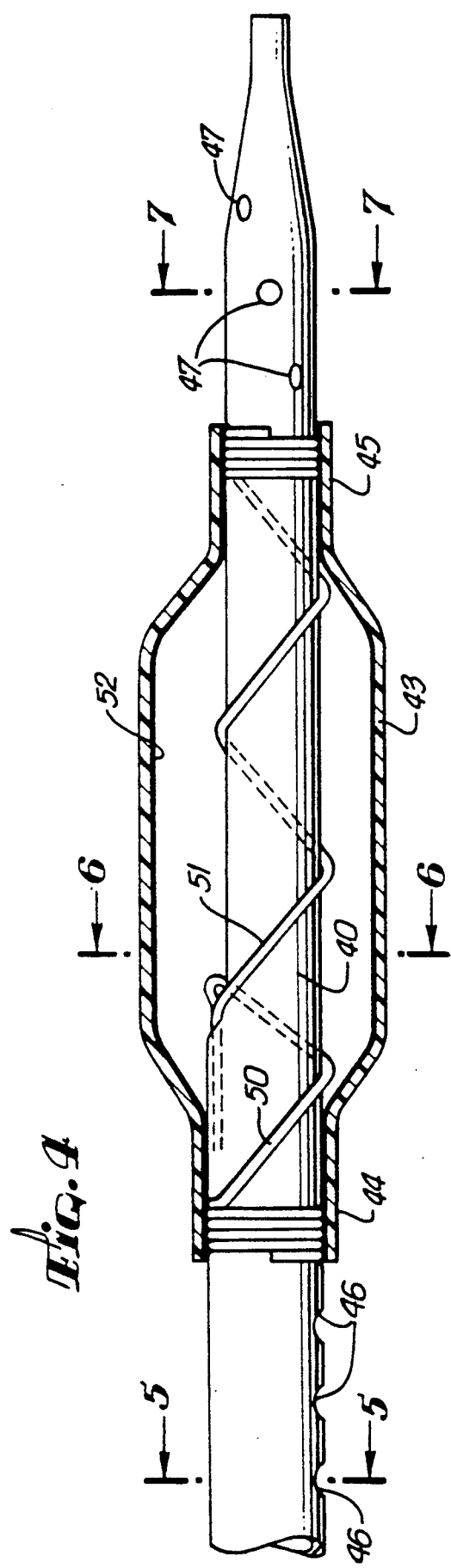
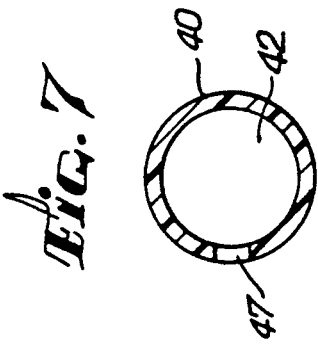
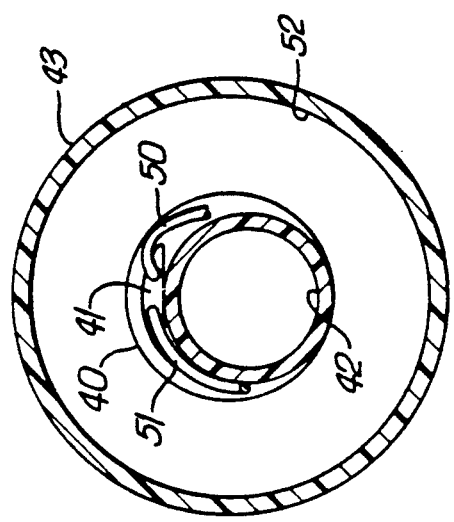
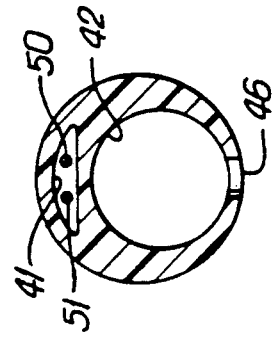

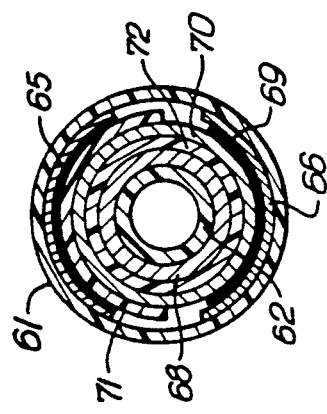
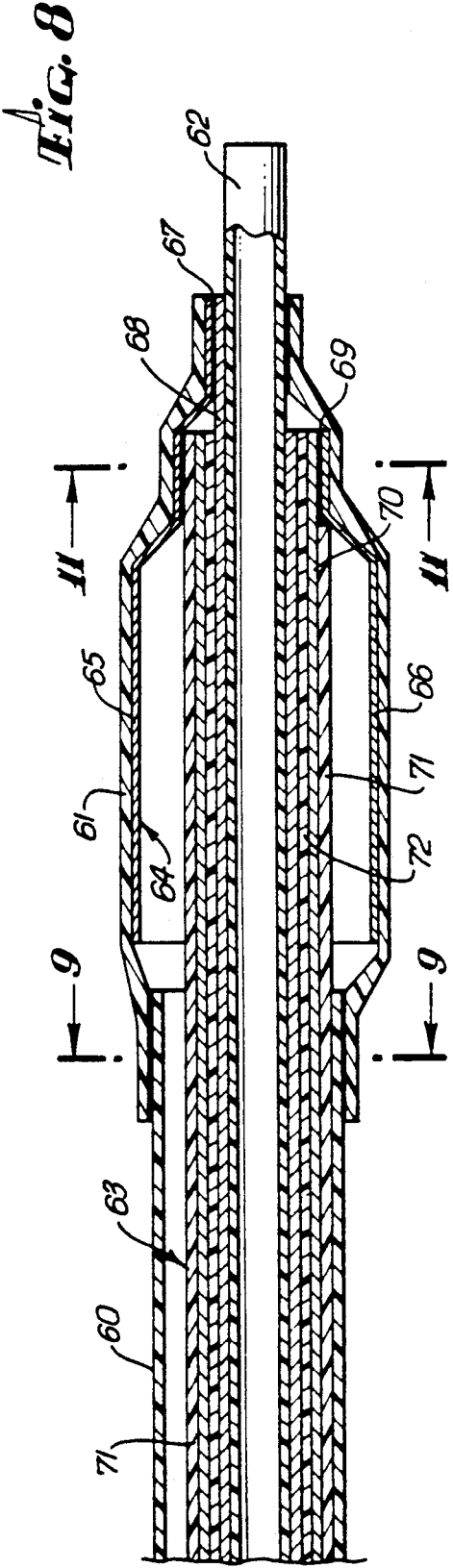
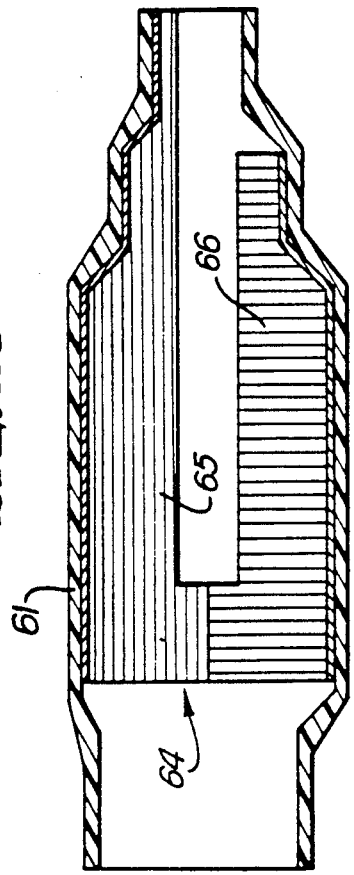
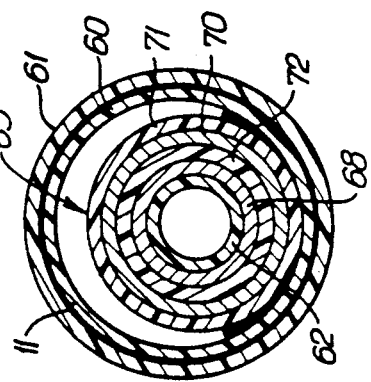

DILATATION CATHETER ASSEMBLY WITH HEATED BALLOON

BACKGROUND OF THE INVENTION

This invention generally relates to a dilatation catheter suitable for angioplasty procedures which has a dilatation balloon with heated working surface and particularly to such a catheter which can perfuse blood distally of the balloon during the inflation thereof.

In typical percutaneous transluminal coronary angioplasty (PTCA) procedures, a guiding catheter having a preformed distal tip is percutaneously introduced into the cardiovascular system of a patient through the brachial or femoral arteries and advanced therein until the distal tip thereof is in the ostium of the desired coronary artery. A guidewire and a dilatation catheter having a balloon on the distal end thereof are introduced through the guiding catheter with the guidewire slidably disposed within an inner lumen of the dilatation catheter. The guidewire is first advanced into the patient's coronary vasculature until the distal end thereof crosses the lesion to be dilated and then the dilatation catheter is advanced over the previously introduced guidewire until the dilatation balloon is properly positioned across the lesion. Once in position across the lesion, the flexible, relatively inelastic balloon is inflated to a predetermined size with radiopaque liquid at relatively high pressures (e.g., greater than about 4 atmospheres) to radially compress the atherosclerotic plaque of the lesion against the inside of the artery wall to thereby dilate the lumen of the artery. The balloon is then deflated so that the dilatation catheter can be removed and blood flow resumed through the dilated artery.

Further details of angioplasty procedures and the devices used in such procedures can be found in U.S. Pat. No. 4,323,071 (Simpson-Robert); U.S. Pat. No. 4,332,254 (Lundquist); U.S. Pat. No. 4,439,185 (Lundquist); U.S. Pat. No. 4,168,224 (Enzmann et al.) U.S. Pat. No. 4,516,972 (Samson); U.S. Pat. No. 4,538,622 (Samson et al.); U.S. Pat. No. 4,554,929 (Samson et al.); and U.S. Pat. No. 4,616,652 (Simpson) which are hereby incorporated herein in their entirety.

Steerable dilatation catheters with built-in or fixed guidewires or guiding elements are used with increasing frequency because such catheters generally have smaller deflated profiles than conventional dilatation catheters with movable guidewires or elements with equivalent balloon size. The lower deflated profile of these catheters allows them to cross tighter lesions and to be advanced much deeper into the patient's coronary anatomy. Moreover, the use of steerable low-profile dilatation catheters can shorten the time for the angioplasty procedure because there is no need to first advance a guidewire across a lesion and then slide a conventional dilatation catheter over the previously advanced guidewire to position the balloon thereof across the lesion. Further details of low-profile steerable dilatation catheters may be found in U.S. Pat. No. 4,582,181 (Samson); U.S. Pat. No. 4,619,263 (Frisbie et al.); U.S. Pat. No. 4,641,654 (Samson et al.); and U.S. Pat. No. 4,664,113 (Frisbie et al.) which are hereby incorporated in their entirety by reference thereto.

Recently, efforts have been made to raise the temperature of the stenotic region during the dilation thereof in the belief that such procedures can minimize restenosis and can prevent abrupt reclosure of the artery when the balloon is deflated and removed. See, for example, U.S. Pat. No. 4,799,479 (Spears) and U.S. Pat. No. 4,643,186 (Rosen) Reference is also made to U.S. Pat. No. 4,662,368 (Hussein et al.) and U.S. Pat. No. 4,807,620 (Strul) which disclose catheters with an enlarged heated probe on the distal tip thereof for opening totally occluded arteries.

However, the prior catheters which applied heat to the atheroma had several disadvantages which can limit their usefulness in humans. For example, the direct irradiation employed in some of these devices can cause extensive coagulation of the blood and thermal injury to the tissue which surrounds the catheter at the treatment site. Moreover, frequently the operator's lack of knowledge of the temperature of the heating element can preclude effective moderation of the thermal treatment level. Additionally, non-uniform heating of the treatment area can create uncertainty whether the treatment area is receiving too much or too little heat. Clinically, these disadvantages have in some cases produced extreme pain, vessel reocclusion or aneurysm. None of the prior devices allowed for long-term dilations at elevated temperature.

What has been needed and heretofore unavailable is a balloon dilatation catheter assembly of simple construction and powered by inexpensive equipment which can quickly and uniformly heat up the atheroma during or following the dilatation thereof and preferably which can also perfuse oxygenated blood distally of the catheter when the balloon is inflated to facilitate effective longterm dilations. The present invention satisfies that need.

SUMMARY OF THE INVENTION

This invention is directed to an improved balloon dilatation catheter which has means for heating the balloon during angioplasty procedures which may also have means to perfuse blood distally of the catheter when the balloon is inflated to facilitate long-term dilations.

The dilatation catheter in accordance with the invention includes an elongated tubular body with an inflatable balloon proximally adjacent the distal end thereof with an inner lumen extending within the tubular body to direct inflation fluid therethrough to the interior of the balloon. A thin conductive layer is provided which is in a radial heat transfer relationship with the working surface (i.e., the outer cylindrical surface) of the balloon and which is coextensive with a substantial portion (i.e., more than 30%, preferably all) of said working surface. In an alternative embodiment, part or all of the balloon itself is formed of conductive material. Electrical conducting means, such as deposited metal layers, foils, or wires may extend longitudinally through the elongated tubular body to electrically connect the thin conductive layer associated with the working surface of the balloon or the conductive balloon to an exterior electrical power source.

The thin electrically conductive layer on the inner surface of the balloon is preferably formed of an electrically conductive polymer, such as polyethylene based polymer, which has incorporated therein conductive metal particles or powder such as silver or gold or other conductive materials such as carbon fibers. Additionally, other metals such as tantalum can be incorporated into the conductive layer to control the resistive heating thereof and to also facilitate fluoroscopic observation of the balloon during the angioplasty procedures.

Electrical power within the radio frequency range is preferred for the rapid and effective heating of the thin conductive layer in a heat transfer relationship with the working surface of the balloon. Such radio frequency power may be effectively delivered to the thin conductive layer by means of a coaxial cable which extends from the proximal end of the catheter through an inner lumen of the tubular body. The coaxial cable generally includes an outer layer of electrically conductive material (e.g., copper, aluminum, silver or gold or alloys thereof) an intermediate layer of dielectric material, such as polytetrafluoroethylene (Teflon) or polyimide, and an inner layer or core formed from electrically conductive materials, such as those described above. The inner conductive layer may be supported by an inner tubular member formed of high-strength plastic material, such as polyimide, which is longitudinally flexible but diametrically relatively rigid. In some embodiments, the inner conductive member may be a solid wire or rod.

In a presently preferred embodiment, the dilatation catheter is provided with a lumen passing through the interior of the balloon with inlet ports proximal to the balloon and discharge ports distal to the balloon to perfuse oxygenated blood to tissue distal to the catheter when the balloon is inflated during angioplasty procedures to permit extended dilatation periods. Long-term dilations of up to 30 minutes or more with a heated balloon allow for lower effective balloon temperatures. While utilization of a thin conductive polymer layer to raise the temperature of the working surfaces of the dilatation balloon is the presently preferred embodiment, alternatives can be used. For example, the thin conductive polymer layer may be replaced by a metallic layer, such as gold, silver, copper, titanium, nichrome, and the like. The conductive layer may be on the interior or exterior surface of the balloon. However, if on the exterior surface, an insulating coating would be required on the metal surface to minimize current flow into the surrounding tissue when the balloon is inflated and heated. Additionally, the balloon member itself can be formed of conductive material, e.g., a conductive carbon loaded plastic such as polyethylene terephthalate. However, as with metallic layers, a thin non-conductive layer is provided on the exterior of the balloon to minimize current flow into surrounding tissue.

The electrical power supplied to the heat up element may be controlled in response to the temperature of the balloon by a suitable feedback control system. The temperature of the outer surface of the balloon is determined directly or indirectly by suitable means and a signal representing the determined value is fed back to a control system which adjusts the output of the power source in response thereto to maintain the desired temperature or other parameter related to the temperature. A simple, inexpensive way to control the electrical power input to the catheter assembly is to calibrate the assembly to heat up to and maintain a desired temperature.

These and other advantages of the invention will become more apparent from the following detailed description of the invention and the attached exemplary drawings.

BRIEF DESCRIPTION OF THE DRAWINGS

FIG. 1 is an elevational view partially in section of a dilatation catheter embodying features of the invention;

FIG. 2 is a transverse cross-sectional view taken along the lines of 2—2 shown in FIG. 1;

FIG. 3 is a transverse cross-sectional view taken along the lines 3—3 shown in FIG. 1; and FIG. 4 is a elevations view partially in section of a perfusion dilatation catheter which embodies features of the invention;

FIG. 5 is a cross-sectional view taken along the lines 5—5 shown in FIG. 4;

FIG. 6 is a cross-sectional view taken along the lines 6—6 shown in FIG. 4;

FIG. 7 is a cross-sectional view taken along the lines 7—7 shown in FIG. 8;

FIG. 8 is a longitudinal view, in section, of an alternative embodiment of a dilatation catheter which embodies features of the invention;

FIG. 9 is a cross-sectional view taken along the line 9—9 shown in FIG. 8;

FIG. 10 is a cross-sectional view similar to FIG. 8 with parts removed to illustrate the layer of conductive material on the interior surface of the balloon;

FIG. 11 is a cross-sectional view taken along the line 11—11 shown in FIG. 8.

DETAILED DESCRIPTION OF THE INVENTION

Figure 12:
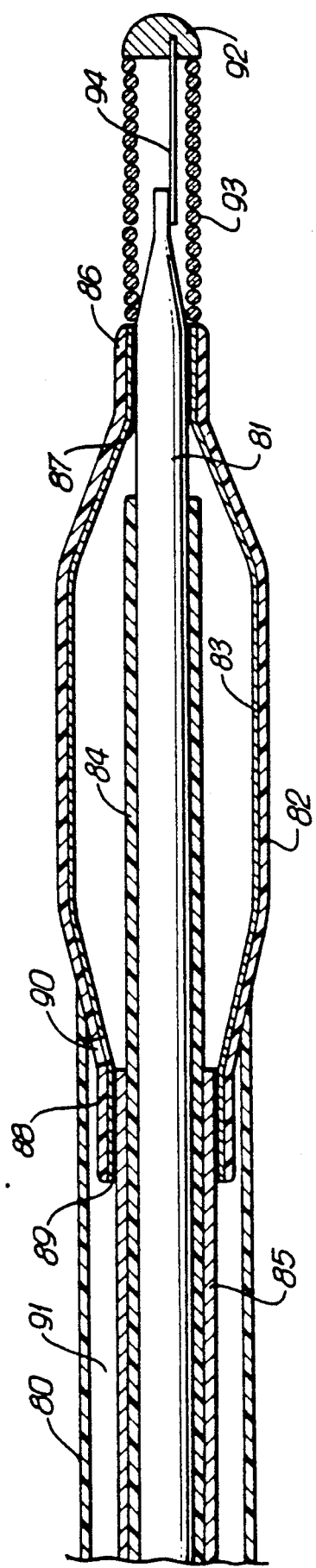
FIG. 12 is a cross-sectional view of a low-profile steerable catheter embodying features of the invention.

Reference is made to FIGS. 1-3 which illustrate a dilatation catheter assembly 10 embodying features of the invention. The catheter assembly 10 generally comprises an outer tubular member 11, an inflatable dilatation balloon 12, and a multi-arm adapter 13 which facilitates directing inflation fluid to the interior of the balloon 12. An inner tubular member 14, preferably formed of nonconducting plastic material, is concentrically disposed within the outer tubular member 11 and has an inner lumen 15 adapted to slidably receive therein a guidewire 16. The guidewire 16 generally comprises an elongated core member 17 and a flexible radiopaque coil 20 on the distal portion thereof. A rounded radiopaque plug 21 is formed on the distal tip of guidewire 16.

The interior surface of the balloon 12 is provided with a thin conductive layer 22 in radial heat transfer relationship therewith, which, when electrical current is passed therethrough, resistively heats up and thereby raises the temperature of the exterior working surface 23 of the balloon 12. Preferably, the entire interior of the working surface of the balloon 12 is coated with the conductive layer 22.

Coaxial cable 24 extends between outer tubular member 11 and inner tubular member 14 and generally comprises an outer conductive layer 25, an inner conductive layer 26 and an annular dielectric layer 27 disposed therebetween. The outer conductive layer 25 is electrically connected to the thin conductive layer 22 at the proximal end or shoulder 30 of the balloon 12 and the inner conductive layer 26 extends through the interior of the balloon 12 and is electrically connected to the thin conductive layer 22 at the distal end or shoulder 31 of balloon 12. Both the outer and inner conductive surfaces 25 and 26 may be coated with a thin insulating layer (not shown) to prevent contact with the inflation medium. An annular passageway 32 extends between the outer tubular member 11 and the outer surface of the coaxial cable 24 to direct inflation fluid from the adapter 13 into the interior of the balloon 12.

The coaxial cable 24 is connected at its proximal end to a suitable electrical power source 33. While such a power source may provide direct current or any suitable frequency of alternating current, in this embodiment the preferred frequency is between about 100 kilohertz and about 100 megahertz. Current frequency in excess of 100 kilohertz is less likely to affect heart muscle contraction and therefore is safer. Typically, the frequency employed is 40 megahertz and the power is about 2 to about 20 watts, preferably about 4 to 12 watts. A suitable radio frequency electrical power source is manufactured by Engineering Research Associates in Tucson, Arizona.

The power source 33 is preferably controlled based directly or indirectly upon the temperature of the balloon 12. In a preferred embodiment, the resistance load of the balloon including the leads thereto is monitored by an ohmmeter and the output of the electrical power source is controlled in response thereto. The signal generated by the ohmmeter 34 is compared with a signal representing a desired set point in a controller 35 which provides a control signal to the power source 33 in a conventional feedback control system, as shown schematically in FIG. 1, to control the output thereof. A wide variety of control systems and strategies may be employed.

In the embodiment shown in FIGS. 1-3, the outer tubular member 11 is preferably formed of polyester such as hytrel, the balloon is formed of a biaxially oriented polyethylene terephthalate, and the inner tubular member 14 is formed of polyimide tubing having a wall thickness of about 0.001 inch. A suitable polyimide tubing is sold by H. V. Technologies in Trenton, Georgia. The conductive layer on the interior surface of the balloon is a polyethylene having an electrically conductive metal such as silver or gold incorporated therein to provide the electrically conductive properties. Powdered tantalum can be incorporated into the coating to control the resistive heating of the layer 22 when electrical current passes therethrough. The presently preferred conductive polymer is CC40A polymer coating material sold by the Emerson & Cummings Company.

Teflon or polyimide tubing, preferably about 0.006 inch thick, is disposed between the inner and outer conductive layers of the coaxial cable 24 as the dielectric layer.

FIGS. 4-7 illustrates another embodiment of a balloon dilatation catheter with a heated balloon which provides for the perfusion of blood distally of the catheter when the balloon thereof is inflated and heated during an angioplasty procedure. The catheter of this embodiment generally comprises a tubular member 40 having a small inner lumen 41, a large inner lumen 42, and a balloon 43 secured by shoulders 44 and 45 thereof to the tubular member. A plurality of inlet ports 46 in the wall of the tubular member 40 are provided proximal to the balloon 43 and a plurality of discharge ports 47 are provided distal thereto. Both the inlet and discharge ports are in fluid communication with the large lumen 42 which extends through the interior of balloon 43. In this manner, when the balloon 43 is inflated and heated for extended periods of time, blood will flow through the inlet ports 46 into lumen 42 and be discharged through ports 47 to supply oxygenated blood to tissue distal to the catheter.

The small lumen 41 contains electrical conductors 50 and 51 for directing electrical power from a source (not shown) exterior to the catheter to the electrically conductive layer 52 provided on the interior of the balloon 43. The small lumen 41 opens into the interior of the balloon 43 with conductor 50 extending to the proximal end or shoulder 44 of the balloon 43 and conductor 51 extends to the distal end or shoulder 45. Generally, the conductors 50 and 51 are wrapped several times about the tubular member 40 underneath the ends or shoulders of the balloon 43 to contact the conductive layer 52 on the inner surface thereof. While the entire interior of the cylindrically shaped portion (the working surface) of the balloon 43 is preferably coated with conductive layer 52, a patterned layer may be used so that both connections thereto can be at the same end of the balloon in order to control the heating of the balloon in a desired fashion.

The passage of electricity through the conductive layer 52 on the interior of the balloon 43 provides sufficient heat to raise the temperature of the exterior working surface 53 of the balloon 43 to the desired levels. In this embodiment, the electrical current may be direct current or current at radio frequencies.

The larger lumen 42 is adapted to receive a guidewire as shown in FIG. 1 to facilitate the advancement of the catheter through the patient's arterial system in a conventional fashion.

FIGS. 8-11 illustrate another embodiment which also has a coaxial cable to transmit electrical power to the heating element of the balloon. The dilatation catheter of this embodiment has an outer tubular member 60 with an inflatable balloon member 61 secured to the distal end thereof and an inner tubular member 62 disposed within the outer tubular member and extending distally through the interior of the balloon. A coaxial cable 63 is disposed about the exterior of inner tubular member 62.

The interior of the balloon is provided with an electrically conductive layer 64 having an upper portion 65 and a lower portion 66. Portions 65 and 66 provide an electrical pathway over the interior of the balloon 61 and allow the ends of the pathway to be electrically connected to coaxial cable 63 at the distal end of the balloon. Upper half 65 is secured by means of electrically conductive adhesive 67 to inner conductive layer 68 of the coaxial cable 63 and the lower half is similarly bonded by electrically conductive adhesive 69 to outer conductive layer 70 of the coaxial cable 63. An outer insulated covering 71 is provided on the exterior of the outer conductive layer 70 and an inner dielectrical layer 72 is provided between the inner and outer conductive layers 68 and 70.

The materials of construction of the prior embodiments are suitable for use in the embodiments shown in FIGS. 8-11.

FIG. 12 illustrates a low-profile steerable dilatation catheter which embodies features of the invention. In this embodiment, the catheter has an outer tubular member 80, an electrically conductive core member 81 disposed within the outer tubular member, and an inelastic inflatable balloon 82 having an electrically conductive layer 83 on the inner surface thereof. The electrically conductive core member 81 has a non-conductive dielectric layer 84 on the exterior surface thereof which in turn has an electrically conductive layer 85 thereon. Both conductive layer 85 and conductive core member 81 may be provided with an insultating outer layer (not shown) to prevent direct contact with the inflation medium or body fluids.

The portions of the core member 81 immediately adjacent the distal end or shoulder 86 of balloon 82 has both the conductive layer 85 and the dielectric layer 84 removed to facilitate the bonding of the core to the conductive layer 83 on the distal end or shoulder 86 of the balloon 82 by means of electrically conductive adhesive 87. The proximal end or shoulder 88 of balloon 82 is similarly secured by electrically conductive adhesive 89 to the outer conductive layer 85. A plurality of passageways 90 are provided in the tapered section of balloon 82 to allow inflation fluid to pass from the annular lumen 91 into the interior of the balloon.

In this embodiment, the distal end of the core member 81 terminates short of the distal plug 92 on the coil 93 and a shaping ribbon 94 is secured to the distal end of core 81 and extends to the plug 92. Other tip constructions may be employed. For example, the core member 81 can extend to the plug 92.

Torquing means (not shown) are provided on the proximal end of the core member 81 as will be appreciated by those skilled in the art to facilitate the advancement of the catheter through a patient's vasculature. The portion of the core member 81 distal to the connection thereof to the distal end of the balloon 82 is preferably coated with insulating material (not shown) in order to prevent the passage of electrical current into surrounding tissue. Both direct current and current at radio frequencies may be employed to heat up the working surface of the balloon as in the other embodiments.

The catheter components of the various embodiments of the invention generally can be made of conventional materials. The tubular member may be formed out of extruded polyester tubing and the balloon may be biaxially oriented polyethylene terephthalate materials. The core member of the guidewire may be formed of stainless steel and the helical coil at the distal tip thereof may be formed in whole or in part of stainless steel or more radiopaque materials, such as platinum, palladium, tungsten, rhenium, molybdenum or alloys thereof.

The conductive layer applied to the interior of the dilatation balloon is preferably formed of a polyethylene based conductive polymer sold under the name of CC40A by the Emerson and Cummings Company which is conductive due to the incorporation therein of silver. To apply the coating, the polymer resin is mixed with suitable solvent, such as capacitor grade toluene, and then applied to coat the interior of the balloon. The balloon with the interior so coated is then placed in an oven at about 90° C. for approximately 2 hours to drive off the solvent and to complete the curing of the polymer material. Coating thicknesses should range from about 0.0002 to about 0.002 inch (0.0051–0.051 mm) with a typical thickness being about 0.001 inch (0.025 mm). Thereafter, the balloon can be secured to the tubular member in a suitable manner such as by heat shrinking the shoulders thereof to the tubular member or by the use of a suitable adhesive such as a cyanoacrylate.

Various modifications can be made to the invention For example, a perfusion lumen can be utilized separate and distinct from the guidewire lumen as shown in Ser. No. 223,088, filed July 22, 1988, which is incorporated herein in its entirety. Additionally, the balloon may be formed in the tubular member by heating and inflating as described in U.S. Pat. No. 4,323,071 (Simpson-Robert). Other modifications and improvements can be made without departing form the scope thereof.

What is claimed is

1. A balloon dilatation catheter having means to apply heat to atheroma within a patient's artery during the dilation thereof, the catheter comprising:
   (a) an elongated tubular member which has an inflation lumen extending therein;
   (b) a flexible, relatively inelastic inflatable balloon on a distal portion of the tubular member which is adapted to receive inflation fluid from the inflation lumen extending therein;
   (c) a singular, electrically conductive pathway which is coextensive with a substantial part of the working portion of the balloon and in radially conductive heat transfer relationship therewith and which has two ends adapted to be connected to an electrical power source in order to pass electrical current therethrough;
   (d) a source for electrical current at a frequency of at least about 100 kilohertz; and
   (e) means connected to the two ends of the electrical conductive pathway to pass electrical current therethrough from the source to resistively heat the conductive pathway and thereby increase the temperature of the part of the working portion of the inflatable balloon which is coextensive with the electrically conductive pathway.

2. The dilatation catheter of claim 1 wherein means are provided to determine the temperature of the surface of the working portion of the balloon in order to control the electrical current to the conductive pathway in response to the temperature determined.

3. The dilation catheter of claim 2 wherein the means to determine the temperature includes means to detect the resistance or inductance load in the conductive pathway of the balloon and the means to pass electrical current thereto.

4. The dilatation catheter of claim 3 including control means to compare the resistance or inductance of the load detected with a desired set point and to adjust the electrical current provided to the conductive pathway in response to the detected resistance or inductance.

5. The dilatation catheter of claim 1 wherein the electrically conductive pathway is a thin conductive layer which is coextensive with at least 30 percent of the outer surface area of the working portion of the inflatable balloon.

6. The dilatation catheter of claim 5 wherein the thin conductive pathway extends continuously in a pattern over the interior surface of the balloon.

7. The dilatation catheter of claim 5 wherein electrical current is supplied to the thin conductive pathway by means of a coaxial cable which extends through tubular body from the proximal end thereof to the inflatable balloon.

8. The dilatation catheter of claim 7 wherein the coaxial cable has inner and outer electrical conducting members and a dielectric disposed therebetween.

9. The dilatation catheter of claim 8 wherein one of said conducting members is electrically connected to one end of the conductive pathway at one end of the balloon and the other conductive member is electrically connected to the other end of the conductive pathway at the other end of the balloon.

10. The dilatation catheter of claim 8 wherein the inner and outer conducting members are formed of electrically conductive wire, foil or deposited layers.

11. The dilatation catheter of claim 10 wherein the electrical conductive members are formed from a material selected from the group consisting of copper, aluminum, silver, gold and alloys thereof.

12. The dilatation catheter of claim 8 wherein the dielectric is a cylindrically shaped member formed of a material selected from the group consisting of poltetrafluoroethylene and polyimide.

13. The dilatation catheter of claim 8 wherein the inner member has a tubular structure with an inner lumen extending therethrough which is adapted to receive a guidewire therein.

14. A balloon dilatation catheter having means to apply heat to atheroma within a patient's artery during the dilatation thereof, comprising:
   (a) an elongated tubular member having an inflation lumen extending therein;
   (b) a flexible, relatively inelastic balloon on the distal portion of the tubular member having an interior which is adapted to receive inflating fluid from the inflation lumen within the tubular member;
   (c) means to elevate the temperature of atheroma within the patient's artery during the dilation thereof when the balloon is inflated;
   (d) a perfusion lumen extending through at least the interior of the balloon;
   (e) one or more inlet ports in the tubular member proximal to the balloon in fluid communication with the perfusion lumen which extends through the balloon; and
   (f) one or more discharge ports in the tubular member distal to the balloon in fluid communication with the perfusion lumen extending therethrough, whereby oxygenated blood may pass through the inlet ports and the perfusion lumen extending through the balloon and out the discharge ports so as to flow distally to the catheter when the balloon is inflated within a patient's artery.

15. A balloon dilatation catheter having means to apply heat to atheroma within a patient's artery during the dilation thereof, the catheter comprising:
   (a) an elongated tubular member having an inflation lumen extending therein;
   (b) a flexible, relatively inelastic inflatable balloon having a cylindrically shaped working section when inflated on a distal portion of the tubular member which is formed at least in part of electrically conductive plastic material and which is adapted to receive inflation fluid from the inflation lumen extending therein to inflate the balloon and press the exterior surface of the working section thereof against atheroma adjacent thereto; and
   (c) means to pass electrical current through the electrically conductive portions of the balloon to resistively heat the balloon and thereby increase the temperature of the exterior surface of the working section of the inflatable balloon.

16. A steerable balloon dilatation catheter having means to apply heat to atheroma within a patient's artery during the dilation thereof, the catheter comprising:
   (a) an elongated tubular member which has an inflation lumen extending therein;
   (b) a flexible, relatively inelastic inflatable balloon on a distal portion of the tubular member which is adapted to receive inflation fluid from the inflation lumen extending therein;
   (c) a torquable guide member which is secured within the catheter and which extends through the interior of the balloon and out the distal end thereof;
   (d) a flexible body which is disposed about the portion of the guide member which extends out the distal end of the balloon;
   (e) a singular, electrically conductive pathway which is coextensive with a substantial part of the working portion of the balloon in a radially conductive heat transfer relationship therewith and which has two ends adapted to be connected to an electrical power source in order to pass electrical current therethrough; and
   (f) means connected to the two ends of the electrical conductive pathway to pass electrical current therethrough from the source to resistively heat the conductive pathway and thereby increase the temperature of the part of the working portion of the inflatable balloon which is coextensive with the electrically conductive pathway.

17. The steerable balloon dilatation catheter of claim 16 wherein the guide member is formed of electrically conductive material and passes electrical current to the electrically conductive pathway.

18. The steerable balloon dilatation catheter of claim 16 wherein the guide member is an inner member of a coaxial cable for passing electrical current to the electrically conductive pathway.

19. The steerable balloon dilatation catheter of claim 18 wherein the coaxial cable extends the length of the elongated tubular member through the inflation lumen thereof.

20. The steerable balloon dilatation catheter of claim 16 wherein the distal end of the tubular member is secured to the exterior of the proximal end of the balloon.

21. The steerable balloon dilatation catheter of claim 20 wherein the proximal end of the balloon has a shoulder which is secured about the coaxial cable and in electrical contact therewith.

22. A method of treating a stenotic region of a patient's artery over an extended period of time, comprising:
   (a) advancing a dilatation balloon catheter through the patient's arterial system until the balloon of the catheter is disposed within the stenotic region;
   (b) inflating the balloon to dilate the stenotic region thereby occluding the patient's artery;
   (c) applying heat to the stenotic region while the balloon is dilating the stenotic region; and
   (d) perfusing blood through a lumen which passes through the interior of the balloon to maintain blood flow to tissue distal to the catheter.

23. The dilatation catheter of claim 8 wherein the inner and outer electrical conducting members are tubular members.

24. The dilatation catheter of claim 23 wherein the inner electrical conducting member has an inner lumen adapted to receive a guidewire.

25. A steerable balloon dilatation catheter having means to apply heat to atheroma within a patient's artery during the dilatation thereof, the catheter comprising:
   (a) an elongated tubular member which has an inflation lumen extending therein;
   (b) a flexible, relatively inelastic inflatable balloon on the distal portion of the tubular member which has a cylindrically shaped working section when inflated and which is adapted to receive inflation fluid from the inflation lumen extending through the tubular member;

(c) an electrically conducting guide member which extends through the interior of the balloon and out the distal end thereof;

(d) a flexible body disposed about and secured to the portion of the guide member which extends out the distal end of the balloon;

(e) an electrically resistive heating means in a heat transfer relationship with the working portion of the balloon;

(f) a source for electrical current at a frequency above about 100 kilohertz; and (f) means to pass electrical current from the source through the guide member to the electrically resistive heating means to raise the temperature thereof and thereby heat the working portion of the inflatable balloon.

26. The steerable dilatation catheter of claim 25 wherein the frequency of the electrical source ranges from about 100 kilohertz to about 100 megahertz.

27. The steerable dilatation catheter of claim 25 wherein the guiding member is secured within the catheter.

28. The steerable dilatation catheter of claim 27 wherein the electrically resistive heating means is a thin layer of conductive material which is secured to the working portion of the inflatable balloon and which is electrically connected to the guide member.

29. A method of dilating a stenotic region of a patient's artery over an extended period of time, comprising:

(a) providing a balloon dilatation catheter having means to apply heat to atheroma within a patient's artery during the dilation thereof, the catheter including:

(i) an elongated tubular member which has an inflation lumen extending therein;

(ii) a flexible, relatively inelastic inflatable balloon on a distal portion of the tubular member which is adapted to receive inflation fluid from the inflation lumen extending therein;

(ii) an electrically conductive means which forms an electrically conductive pathway for electrical current coextensive with a substantial part of the working portion of the balloon and in radially conductive heat transfer relationship therewith;

(iii) a source for electrical current at a frequency at least about 100 kilohertz; and (iv) means to pass the electrical current from the source through the electrically conductive pathway to resistively heat the conductive means and thereby increase the temperature of the working portion of the inflatable balloon;

(b) advancing the dilatation balloon catheter through the patient's arterial system until the balloon of the catheter is disposed within the stenotic region;

(c) inflating the balloon to dilate the stenotic region thereby occluding the patient's artery;

(d) applying heat to the stenotic region while the balloon is inflated to dilate the stenotic region by directing the electrical current from the source thereof through the electrical conducting pathway to resistively heat up the conductive means and thereby the working portion of the balloon.

* * * * *